US006348609B1

(12) United States Patent
Rombi

(10) Patent No.: US 6,348,609 B1
(45) Date of Patent: Feb. 19, 2002

(54) METHOD FOR OBTAINING AN OIL THAT IS RICH IN HYDROXYOCTADECADIENOIC FATTY ACIDS (HODE) OR THE ESTERS THEREOF FROM A MIXTURE CONTAINING LINOLEIC ACID OR THE ESTERS THEREOF

(75) Inventor: Max Rombi, Bordighera (IT)

(73) Assignee: Laboratoires Arkopharma, Carros (FR)

( * ) Notice: Subject to any disclaimer, the term of this patent is extended or adjusted under 35 U.S.C. 154(b) by 0 days.

(21) Appl. No.: 09/647,474

(22) PCT Filed: Jan. 28, 2000

(86) PCT No.: PCT/FR00/00208

§ 371 Date: Nov. 28, 2000

§ 102(e) Date: Nov. 28, 2000

(87) PCT Pub. No.: WO00/44863

PCT Pub. Date: Aug. 3, 2000

(30) Foreign Application Priority Data

Jan. 29, 1999 (FR) .............................. 99 01078

(51) Int. Cl.[7] .............................. C07C 51/00
(52) U.S. Cl. ................... 554/132; 514/552; 514/556; 514/909
(58) Field of Search .................... 554/132; 514/58, 514/552, 909

(56) References Cited

FOREIGN PATENT DOCUMENTS

| EP | 0 097 059 | 12/1983 |
| EP | 0 437 694 | 7/1991 |
| EP | 437694 | * 7/1991 |

OTHER PUBLICATIONS kuklev et al., Chem. and Physics of Lipids, vol. 85, No. 2, pp. 125–134, 1997.*

D.V. Kuklev et al, "Synthesis of keto– and hydroxydienoic compounds from linoleic acid" Chemistry and Physics of Lipids, vol. 85, No. 2, 1997, pp. 125–134, XP000852628, Limerick, IR ISSN: 0009–3084, p. 125, Abstract, p. 132, column 1, paragraph 1, p. 133, column 2, last paragraph.

Patent Abstracts of Japan, V ol. 012, No. 005 (C–467), Jan. 8, 1988 & JP 62 164620 A (Tsumura Juntendo Inc), Jul. 21, 1987, abstract.

N. Marx et al, "PPARgamma activation in human endothelial cells increases plasminogen activator inhibitor type–1 expression" Arteriosclerosis, Thrombosis, and Vascular Biology, vol. 19, No. 3, 1999, pp. 546–551, XP000909225, ISSN: 1079–5642, p. 546, column 1, paragraph 1—p. 546, column 1, paragraph 1, p. 550, column 1, paragraph 2—column 2, last paragraph.

* cited by examiner

Primary Examiner—Deborah D. Carr
(74) Attorney, Agent, or Firm—Burns, Doane, Swecker & Mathis, L.L.P.

(57) ABSTRACT

A method for obtaining an oil that is rich in hydroxyoctadecadienoic(HODE) fatty acids or the esters thereof. According to the inventive method, controlled oxidation of the linoleic acid and/or the linolenic acid or the esters thereof is performed in the presence of an oxidation catalyst. The oxidation is terminated when the HODE content or total ester content is more than 5 % and/or the 9-hydroxy-10,12-octadecadienoic(9-HODE) acid isomer or ester content is more than 1.5 % and reduction occurs for the hydroperoxides formed during the oxidation reaction by a reducer. The invention can be used as a medicament, food supplement or cosmetic.

17 Claims, No Drawings

METHOD FOR OBTAINING AN OIL THAT IS RICH IN HYDROXYOCTADECADIENOIC FATTY ACIDS (HODE) OR THE ESTERS THEREOF FROM A MIXTURE CONTAINING LINOLEIC ACID OR THE ESTERS THEREOF

The present invention relates to a process for preparing hydroxyoctadecadienoic acids, more particularly 9-hydroxy-10,12-octadecadienoic acid and 13-hydroxy-9,11-octadecadienoic acid, and a mixture thereof, as well as the isomers thereof such as 9(R/S)-hydroxy-10E,12Z-octadecadienoic acid, optionally in the form of the esters thereof, more particularly in the form of the ethyl ester thereof.

In the description which follows, hydroxyoctadecadienoic acid is referred to as HODE.

The invention relates to a process for preparing HODE by controlled oxidation of linoleic acid and/or of linolenic acid, followed by reduction.

The invention also relates to a process for preparing HODE from triglycerides that are rich in linoleic acid and/or linolenic acid or from linoleic acid and/or lenolenic acid in the form of free fatty acid or in the form of an ester or salt, for example in the form of the ethyl ester.

The invention also relates to a drug, in particular for treating obesity, containing HODE as active principle and pharmacologically acceptable supports.

The invention also relates to a dietary supplement containing HODE, in particular for treating obesity.

The invention furthermore relates to a cosmetic product containing HODE and cosmetically acceptable supports, more particularly for the localized treatment of excess weight and its consequences on the appearance of the skin, such as "orange-peel" skin, nodes of fat and steatomery.

It is generally accepted that the increase in the prevalence of excess weight and obesity in developed countries is due to an unsuitable diet, both as regards the excessive overall calorific intake and as regards an excessive fat content in this calorific intake. This very high fat content in the diet (estimated on average at close to 50% of the energy intake) may be reduced in the case of low-calorie diets in which the fats are greatly reduced.

However, the fats cannot be reduced to less than 30% of the energy intake since, not only do they play an important role in the texture and taste perception of foods, but also a minimum amount is necessary in the diet, in particular for the biosynthesis of essential fatty acids and hormones, and for the renewal of membrane phospholipids.

An essential axis of the research concerning the treatment of obesity has for several decades thus been the selection of "good fats", i.e. fats which are not stored in the body, but used as a source of energy. In this context, it has been established that the nature of the fatty acids of which fats are composed plays a fundamental role in their metabolism. By way of example, short-chain fatty acids are more heat generating than long-chain fatty acids.

It has been possible to observe that the chain length of fatty acids has a direct influence on the energy expenditure and thus on their storage in the body.

One of the objects of the invention is to find a molecule for regulating the lipolytic activity of adipocytes, i.e. a molecule capable of hydrolyzing the triglycerides stored in adipocytes into free fatty acids and glycerols.

It is known that adrenaline and caffeine are two molecules that are known for their lipolytic effects. These are, in particular, molecules which increase the levels of cyclic adenosine monophosphate (cAMP), which is the first step in the activation of lipolysis.

One of the aims of the invention is thus, inter alia, to find a molecule which activates lipolysis to a greater extent than caffeine or adrenaline, by virtue of stimulating the production of cAMP by adipocytes.

Another aim of the invention is to provide a lipolytic molecule synthesized, simply and efficiently, from products commonly found in nature.

The inventors have discovered, surprisingly, that hydroxyoctadecadienoic (HODE) fatty acid derivatives have advantageous heat-generating properties without resulting in toxicity, and in particular 9-hydroxyoctadecadienoic acid in free acid form or in the form of esters or salts.

The invention thus relates to a process for obtaining an oil that is enriched in hydroxyoctadecadienoic (HODE) fatty acid and in particular in 9-hydroxyoctadecadienoic acid (9-HODE), or esters or salts thereof, from an oily mixture containing linoleic acid and/or linolenic acid, or esters or salts thereof, characterized in that a controlled oxidation of linoleic acid and/or of linolenic acid, or of esters thereof, is carried out in the presence of an oxidation catalyst, the oxidation being stopped when the total content of HODE, or of esters thereof, is greater than at least 5% and/or the content of 9-hydroxy-10,12-octadecadienoic acid (9-HODE) isomer, or of esters thereof, is greater than at least 1.5%, and in that the hydroperoxides formed during the oxidation reaction are reduced with a reducing agent.

The starting oily mixture is a plant oil containing more than 40% by weight of linoleic acid and/or of linolenic acid in the form of triglycerides, such as corn oil, borage oil, safflower oil, soybean oil, evening primrose oil, sunflower oil, blackcurrant pip oil, wheatgerm oil, hemp oil, marrow seed oil or flax oil.

The starting oily mixture is an oily mixture containing more than 40% by weight of linoleic acid and/or of linolenic acid, and preferably containing 75% ethyl linoleate.

The final content of total HODE or of 9-HODE in the enriched oil is at least 5%, or 1.5% respectively, by weight.

Preferably, the final content of total HODE or of 9-HODE in the enriched oil is respectively between 10% and 12% by weight and between 2.2% and 2.5% by weight.

The oxidation catalyst is an iron or copper halide, preferably $FeCl_3$.

The reducing agent is preferably $NaBH_4$.

The invention also relates to the oil enriched in hydroxyoctadecadienoic (HODE) fatty acid or esters or salts thereof, obtained as described above.

Furthermore, the invention relates to a drug for treating obesity, containing, as active principle, 9-hydroxyoctadecadienoic (9-HODE) fatty acid or pharmacologically acceptable esters or salts thereof, preferably in the form of enriched oil obtained as described above.

The invention also relates to a dietary supplement for treating obesity, containing, as active principle, 9-hydroxyoctadecadienoic (9-HODE) fatty acid or pharmacologically acceptable esters or salts thereof, preferably in the form of enriched oil obtained as described above.

The invention furthermore relates to a cosmetic product for treating obesity, containing, as active principle, 9-hydroxyoctadecadienoic (9-HODE) fatty acid or cosmetologically acceptable esters or salts thereof, preferably in the form of enriched oil obtained as described above.

According to the invention, hydroxyoctadecadienoic acid (HODE) is obtained by controlled oxidation of linoleic acid and/or of linolenic acid. These fatty acids are present in many plant oils.

For example, the following plant oils contain more than 40% linoleic acid in the form of triglycerides: borage oil, safflower oil, soybean oil, evening primrose oil, sunflower oil, blackcurrant pip oil, wheatgerm oil, hemp oil, marrow seed oil, flax oil.

According to a first embodiment of the invention, the HODE can be obtained from triglycerides that are rich in linoleic and/or linolenic acid. This process is advantageous since it allows the use of a natural plant oil which is thus entirely suitable for oral use, but has the drawback of considerably limiting the final content of 9-HODE isomer. Specifically, the fact that the linoleic and/or linolenic acid is in the form of glycerides limits the oxidation effect, which is the first step in the preparation of 9-HODE, but above all the linoleic acid content of about 40 to 50% among the mixture of fatty acids in the natural oil limits the final content of 9-HODE.

The structure of the starting material is a linoleic acid triglyceride or a linoleic acid ester of general formula (I) below:

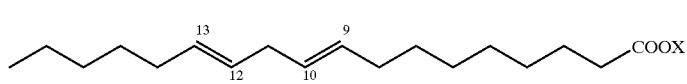

(I)

in which X is a triglyceryl residue or an Et (ethyl) residue or any other $C_1$–$C_6$ lower alkyl residue.

Such a compound has a double bond in position 9,10 and a double bond in position 12,13. Controlled oxidation produces, according to the invention, the compounds of general formulae (II) and (III) below:

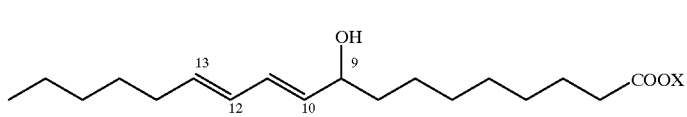

(II)

which is the glyceryl or alkyl ester of 9-hydroxy-10,12-octadecadienoic acid, or

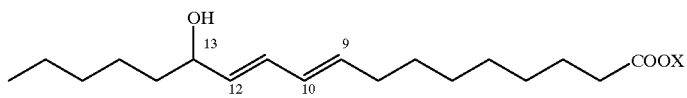

(III)

which is the glyceryl or alkyl ester of 13-hydroxy-9,11-octadecadienoic acid.

Controlled oxidation of (I) thus gives a mixture of isomers (II) and (III).

Linolenic acid exists in two forms: α-linolenic acid (or (Z,Z,Z)-9,12,15-octadecatrienoic acid) and γ-linolenic acid (or (Z,Z,Z)-6,9,12-octadecatrienoic acid).

The oxidation reaction is carried out in the presence of an oxygenation catalyst such as an iron or copper halide, preferably $FeCl_3$. The reaction has a duration ranging from 12 to 78 hours and a temperature of between −20° C. and 40° C., at atmospheric pressure and/or under reduced pressure. The degree of oxidation is monitored by different criteria:

assay of the hydroxides formed by gas chromatography;
change in the ultraviolet absorbance at 235 ±5 nm;
variation of the refractive index.

When the weight percentage of compound (II) (9-HODE) or the weight percentage of the mixture of compounds (II) and (III) reaches from 1 to 20%, the mixture is reduced, i.e. the hydroperoxides formed during the oxidation are reduced. An ethanolic solution of $NaBH_4$ or an ethanolic solution of any other reducing agent is used, which is added portionwise to the reaction mixture. The temperature of the mixture is maintained between 4 and 25° C. The reduction is stopped when the temperature becomes constant. The reaction medium is neutralized to pH 6–7 by adding an acid solution, preferably a solution of a pharmacologically and/or cosmetologically acceptable acid, for example citric acid.

Compounds (II) and (III) are extracted with hexane or any other organic solvent capable of dissolving them. The organic phase is washed with water until neutral.

The organic phase is then dried over anhydrous sodium sulphate or anhydrous magnesium sulphate.

The filtrate is then evaporated under vacuum.

The product obtained is a pale yellow oily liquid having a slightly aromatic odor. It has a total content of compounds (II) and (III) (determined by gas chromatography) of greater than 5% by weight and a content of compound (II) [9(R/S)-hydroxy-10E,12Z-octadecadienoic acid or 9(R/S)-hydroxy-10E,12Z-octadecadienoic acid ester] of greater than 1.5% by weight.

According to a second embodiment of the invention, which is preferred, the starting material is an oily mixture containing 75% by weight of ethyl linoleate.

The principle is the same as that described for the first embodiment of the invention. A selective oxidation of ethyl linoleate is carried out, followed by a reduction of the hydroperoxides formed and a purification by successive washes. A pale yellow oil of specific odor is obtained, containing about 2.5% by weight of 9-hydroxy-10E,12Z-octadecadienoic acid (in ethyl ester form) and 12% of a mixture of compounds (II) and (III) (in the form of ethyl esters). The hydroxyl function may be in position 9 or 13 and the double bonds in conjugated form at 10,12 (trans,trans and cis,trans) and in position 9,11 (trans,trans and cis,trans).

Example for the Preparation of an Oil Enriched in HODE Starting with a Mixture Containing 75% Ethyl Linoleate 1. Oxidation 500 g of 75% ethyl linoleate are introduced into a thermostatically controlled reactor. 0.500 g of anhydrous $FeCl_3$ (oxidation catalyst) is added and the mixture is brought to a temperature in the region of 25–27° C. and maintained under uniform stirring.

Oxygen (technical grade) is bubbled into the reaction medium using a stainless-steel or bronze filter with a porosity of 2 to 4 $\mu$m (such as an HPLC filter or a particle filter for gases). This fine bubbling is maintained at a flow rate of 1 litre/min for 48 to 72 hours.

The degree of oxidation is monitored either:

by measuring the refractive index at 20° C. on the crude product in the reaction medium;

by measuring the UV absorbance at 234 nm (detection of the conjugated dienes); or by assay by gas chromatography after reduction of the sample taken in the reactor.

The oxidation is stopped when the 9-HODE and/or total HODE content are, respectively, from 2.2% to 2.5% and from 10% to 12%.

2. Reduction 0.16 g of antioxidant such as Coviox T70 is added to the hydroperoxide-containing mixture. An ethanolic solution of $NaBH_4$ at a concentration of 2% (weight/volume) is prepared and is cooled to about 4° C. This reductive solution is added slowly and in several portions to the hydroperoxide-containing mixture, while maintaining the reaction medium at a temperature below 25 ° C. (about 20° C.).

The reduction phase is stopped when the temperature is constant when stirring is maintained at room temperature (about 1 hour).

The reduction reaction releases hydrogen.

3. Neutralization to pH 6–7

100 ml of a 25% solution of citric acid in ethanol are added slowly to the reaction mixture with stirring. A release of hydrogen and occasionally a precipitation of sodium citrate may occur.

4. Extraction, separation by settling, washing and drying 500 ml of n-hexane and then 500 ml of water are added to the reaction medium, with rapid stirring, and the mixture is allowed to separate by settling. After separation of the two phases, the organic phase is recovered.

This organic phase is washed until the washing waters are neutral, and is then dried by filtration over about 140 g of anhydrous sodium sulphate.

5. Evaporation 0.16 g of antioxidant (Coviox T70) is added to the organic phase and the n-hexane is evaporated off under vacuum at a temperature in the region of 50° C. to 60° C.

6. Packaging and storage

The oil obtained is stored in a brown glass container or in a drum under nitrogen and at a temperature below 10° C.

Pharmacological Properties

The aim of the invention is to find a molecule that is active on lipolysis, i.e. that is capable of promoting the hydrolysis of triglycerides stored in adipocytes, the free fatty acids thus released then being metabolized.

Pharmacological Study on Human Adipocytes

The aim of this study is to study the effect of 9-HODE on the production of cAMP (cyclic adenosine monophosphate) which is a lipolysis activator, in human adipocytes. The effect of 9-HODE is studied relative to that of adrenaline and caffeine which are two molecules that are known for their lipolysis-stimulating effects.

It was found that a 9-HODE concentration of $10^{-4}$ M leads to an increase in cAMP which is equivalent to that of caffeine $10^{-3}$ M and greater than that obtained, irrespective of the concentration, by adrenaline.

At a 9-HODE concentration of $10^{-3}$ M, the concentration of cAMP is 10 times greater than that obtained with caffeine (7.940 femtomol of cAMP/million adipocytes against 799).

These results make it possible to conclude that 9-HODE is, in vitro, a powerful lipolysis activator by means of stimulating the greater production of cAMP by adipocytes than that of the caffeine and adrenaline molecules.

Studies on Rats

The study is carried out on twelve rats which are first subjected to a restricted food intake (simulation of a diet) for two weeks, and then receive a normal food intake (regain of weight) optionally combined with the administration of a sunflower oil treated according to the process of the present invention and containing 2% by weight of 9-HODE. A control group is used which receives sunflower oil lacking 9-HODE. After treatment for eleven days, the fat mass in the two groups is measured.

The results obtained show, in the group receiving the sunflower oil containing 2% by weight of 9-HODE, that the fat mass is significantly ($p<0.001$) 25% less than that measured in the placebo group (21.8 g compared with 29.5 g in the control group).

The oral administration of sunflower oil containing 2% by weight of 9-HODE thus makes it possible to statistically significantly reduce the fat mass in rats treated with this plant oil.

Study of Skin Penetration

A study of skin penetration is carried out in vitro on human skin with Franz cells. These cells comprise a surface area of human skin of 1.76 $cm^2$ on which is placed 800 $\mu$g of 9-HODE. After 6 hours of contact, an assay of the 9-HODE is carried out by gas chromatography at the surface of the human skin sample, in the epidermis, in the dermis and in the receiving phase.

| | |
|---|---|
| surface of the skin: | 33% |
| epidermis: | 11% |
| dermis: | 32% |
| receiving phase: | 24% |

9-HODE thus has high skin-penetrating power, thus allowing it to act directly on adipocytes.

Clinical Studies of 9-HODE

Clinical Study Evaluating the Efficacy of a Cosmetic Gel Containing 0.5% 9-HODE

A clinical study is carried out on twenty women exhibiting an excess of adipose tissue on the thighs ("steatomery"). The volunteers applied a gel containing 0.5% 9-HODE onto each thigh, twice a day for one month. The efficacy criterion is the measurement of the circumference of the thigh at two levels.

The results obtained demonstrate the efficacy of the product since a 6 mm reduction in circumference at the upper level of the thigh and a 5.4 mm reduction in circumference at the lower level of the thigh are observed, these two reductions being statistically very significant.

Clinical Study Evaluating the Efficacy of a Cosmetic Gel Containing 1.5% 9-HODE Another study was carried out on 21 women exhibiting excess fat on the thighs. The product studied was a cosmetic solution containing 1.5% HODE and made it possible to show a statistically significant reduction in the perimeter of the thighs of 7 mm by the 12th day of application and of 10 mm after 24 days of application. Moreover, 80% of the women observed a marked improvement in the firmness of the skin and a reduction in the "orange-peel" skin appearance and in the nodes of fat.

Clinical Study Evaluating the Increase in Heat Generation After Single Oral Intake of 9-HODE A study is carried out on ten healthy volunteers who ingested the following products at random:

| | |
|---|---|
| sunflower oil: | 20 g |
| sunflower oil: | 20 g containing 2% 9-HODE. |

Each individual receives, at an interval of one week, each of the products in a random order (cross-over protocol). The volunteers spend two hours in a calorimetric chamber (basal energy expenditure) and then absorb one of the two products in the course of a standardized 800 kcal meal and remain in the calorimetric chamber for 6 hours (energy expenditure after treatment).

The average energy expenditure (kjoule/minute) with the two products is:

| | Basal energy expenditure | Energy expenditure after treatment |
|---|---|---|
| Sunflower oil | 5.76 | 6.35 |
| Sunflower oil +2% 9-HODE | 5.68 | 6.82 |

The difference in energy expenditure after treatment is statistically significant ($p<0.01$). This increase in heat generation of close to 8% is particularly advantageous for the treatment of obesity.

The invention thus makes it possible to treat obesity via the oral route and localized weight excess via the topical route. Via the oral route, 9-HODE can be administered in acid form or in the form of triglyceride. Via the topical route, 9-HODE is preferably administered in free acid form.

9-HODE can be administered as a dietary supplement in the form of gel capsules, tablets, a drinkable solution, lozenges, chewing gum, etc. and/or in foods. 9-HODE can be used pure or diluted in creams, gels, sticks, ointments, etc.

When applied to areas of excess weight, it makes it possible to have a direct action on adipocytes. 9-HODE can be administered as a drug systemically or topically for the treatment of obesity. The administration doses are, for example, from 50 to 5000 mg/day via the oral route and from 0.1 to 100% via the local route.

What is claimed is:

1. A method for treating obesity, comprising administering an effective amount of 9-hydroxyoctadecadienoic (9-HODE) fatty acid or pharmacologically acceptable esters or salts thereof to a patient in need of such treatment.

2. A method for the localized treatment of excess weight and of its consequences on the appearance of the skin comprising administering an effective amount of 9-hydroxyoctadecadienoic (9-HODE) fatty acid or cosmetically acceptable esters or salts thereof to a person in need of such treatment.

3. A process for obtaining an oil that is enriched in hydroxyoctadecadienoic (HODE) fatty acid or esters thereof from an oily mixture containing linoleic acid or esters thereof, comprising oxidizing in a controlled manner linoleic acid and/or of linolenic acid, or of esters thereof, in the presence of an oxidation catalyst, the oxidation being stopped when the total content of HODE, or of esters thereof, is greater than 5% and/or the content of 9-hydroxy-10,12-octadecadienoic acid (9-HODE) isomer, or of esters thereof, is greater than 1.5%, wherein the hydroperoxides formed during the oxidation reaction are reduced with a reducing agent.

4. The process according to claim 3, wherein the starting oily mixture is a plant oil containing more than 40% by weight of linoleic acid and/or of linolenic acid in the form of triglycerides.

5. The process according to claim 3, wherein the starting oily mixture is an oily mixture containing more than 40% by weight of linoleic acid and/or of linolenic acid, in the form of the ethyl ester.

6. The process according to claim 3, wherein the final content of total HODE or of 9-HODE in the enriched oil is at least 5%, or 1.5% respectively, by weight.

7. The process according to claim 3, wherein the final content of total HODE or of 9-HODE in the enriched oil is respectively between 10% and 12% by weight and between 2.2% and 2.5% by weight.

8. The process according to claim 3, wherein the oxidation catalyst is an iron or copper halide.

9. The process according to claim 3, wherein the reducing agent is $NaBH_4$.

10. An oil enriched in 9-hydroxyoctadecadienoic (9-HODE) fatty acid or esters or salts thereof, obtained by the process according to claim 3.

11. A pharmaceutical composition for treating obesity, comprising an effective amount of 9-hydroxyoctadecadienoic (9-HODE) fatty acid or pharmacologically acceptable esters or salts thereof and a pharmaceutically acceptable carrier.

12. A cosmetic composition for the localized treatment of excess weight and of its consequences on the appearance of the skin comprising an effective amount of 9-hydroxyoctadecadienoi acceptable esters or salts thereof and a cosmetically acceptable carrier.

13. The process according to claim 4, wherein said starting oily mixture comprises corn oil, borage oil, safflower oil, soybean oil, evening primrose oil, sunflower oil, blackcurrant pip oil, wheatgerm oil, hemp oil, marrow seed oil or flax oil.

14. The process according to claim 5, wherein said oil mixture contains 70% ethyl linoleate.

15. The process according to claim 8, wherein said oxidation catalyst is $FeCl_3$.

16. The process according to claim 11, wherein said 9-HODE fatty acid is in the form of an enriched oil.

17. The composition according to claim 12, wherein said 9-HODE fatty acid is in the form of enriched oil.

* * * * *

UNITED STATES PATENT AND TRADEMARK OFFICE
CERTIFICATE OF CORRECTION

PATENT NO.   : 6,348,609 B1
DATED        : February 19, 2002
INVENTOR(S)  : Max Rombi It is certified that error appears in the above-identified patent and that said Letters Patent is hereby corrected as shown below:

<u>Column 8,</u>
Line 52, change "9-hydroxyoctadecadienoi" to -- 9-hydroxyoctadecadienoic (9-HODE) fatty acid or cosmetically --.
Line 59, change "70%" to -- 75% --.

Signed and Sealed this

Tenth Day of September, 2002

Attest:

JAMES E. ROGAN
Attesting Officer    Director of the United States Patent and Trademark Office